US00PP10114P

United States Patent [19]

Gale

[11] Patent Number: Plant 10,114

[45] Date of Patent: Nov. 11, 1997

[54] APPLE TREE 'GALE GALA'

[75] Inventor: Wallace F. Gale, Malaga, Wash.

[73] Assignee: Van Well Nursery, Inc., Wenatchee, Wash.

[21] Appl. No.: 585,500

[22] Filed: Jan. 16, 1996

[51] Int. Cl.[6] ..... A01H 5/00

[52] U.S. Cl. ..... Plt./34.1

[58] Field of Search ..... Plt./34.1

[56] References Cited

U.S. PATENT DOCUMENTS

P.P. 4,121 10/1977 Ten Hove .
P.P. 6,172 5/1988 Creech .
P.P. 7,396 12/1990 Cooper .
P.P. 7,589 7/1991 Fulford et al. .
P.P. 8,460 11/1993 Knottenbelt .
P.P. 8,621 3/1994 Olsen et al. .
P.P. 8,673 4/1994 Waliser .
P.P. 9,681 11/1996 Olsen et al. ..... Plt./34.1

*Primary Examiner*—James R. Feyrer
*Attorney, Agent, or Firm*—Christensen O'Connor Johnson & Kindness

[57] ABSTRACT

A new and distinct variety of apple tree which originated as a whole-tree sport mutation of the Tenroy cultivar Gala (U.S. Plant Pat. No. 4,121) apple tree, characterized by: apples that color early with dark red striping over solid red undercolor; red calyx end and red leaf midvein.

5 Drawing Sheets

The invention relates to a new and distinct variety of apple tree, *Malus domestica*, which originated as a whole-tree sport mutation of the Tenroy cultivar Gala (U.S. Plant Pat. No. 4,121) apple tree.

DISCOVERY AND ASEXUAL REPRODUCTION OF THE TREE

The new variety was discovered by Wallace F. Gale in 1991 at his orchard located at 3796 Searles Road, Malaga, Wash. The subject tree was found in a cultivated Royal Gala® (Tenroy cv.) orchard block.

Mr. Gale was attracted to the tree by the noticeably earlier red color of the fruit, especially in comparison to fruit on the adjacent Royal Gala® (Tenroy cv.) trees, and the standard and uniform red coloring of all fruit on the subject tree. The new variety also exhibits deeper red fruits than Tenroy cv. This color is darker red than that of other Gala sports, including the Waliser cv. (U.S. Plant Pat. No. 8,673) and Olsentwo Gala (marketed as Pacific Gala—U.S. Plant Pat. No. 9,681). The new variety colors 98 to 100 percent red blush undercolor with darker red striping covering the blush. It also colors fully at the calyx end of the apple, which is not the case with Waliser cv., Olsentwo Gala, or other Red Gala sports. The new variety bears fruit that color at the same time during the growing season, in contrast to the Tenroy cv. fruit that color at different times during the growing season.

Asexual reproduction of the Gale Gala tree was successfully accomplished in August 1992 at which time a second generation was top budded onto Oregon Spur II® Red Delicious (Wells & Wade cv., U.S. Plant Pat. No. 4,819) trees located at Mr. Gale's Malaga orchard. Later that month, 150 rootstocks were budded to Gale Gala at the Van Well Nursery growing fields in Quincy, Wash. The 150 finished trees were planted and grown at Mr. Gale's Malaga orchard in Spring 1994. Third generation trees have also been asexually propagated from the second generation trees. All the fruit borne on the second generation and third generation trees have been identical to the fruit borne on the original whole-tree sport. All the second generation and third generation fruit has exhibited the 98 to 100 percent full, dark red undercolor with darker red striping, and color evenly at the same time during the growing season.

Moreover, the fruit still maintains the taste and texture of apples from the parental Royal Gala® (Tenroy cv.) trees.

BRIEF DESCRIPTION OF THE DRAWINGS

The accompanying photographs show the following distinguishing characteristics of this new variety.

SUMMARY OF THE TREE

Figure 1:
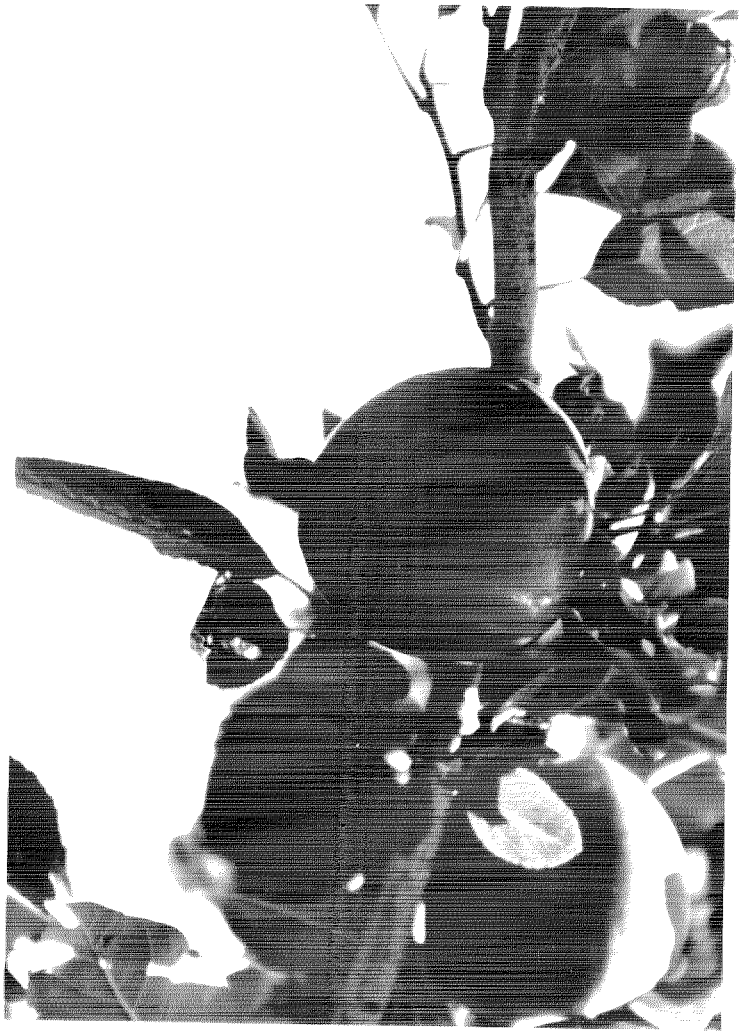
FIG. 1 shows the dark red striping over solid red undercolor of the fruit of this new variety.
Figure 2:
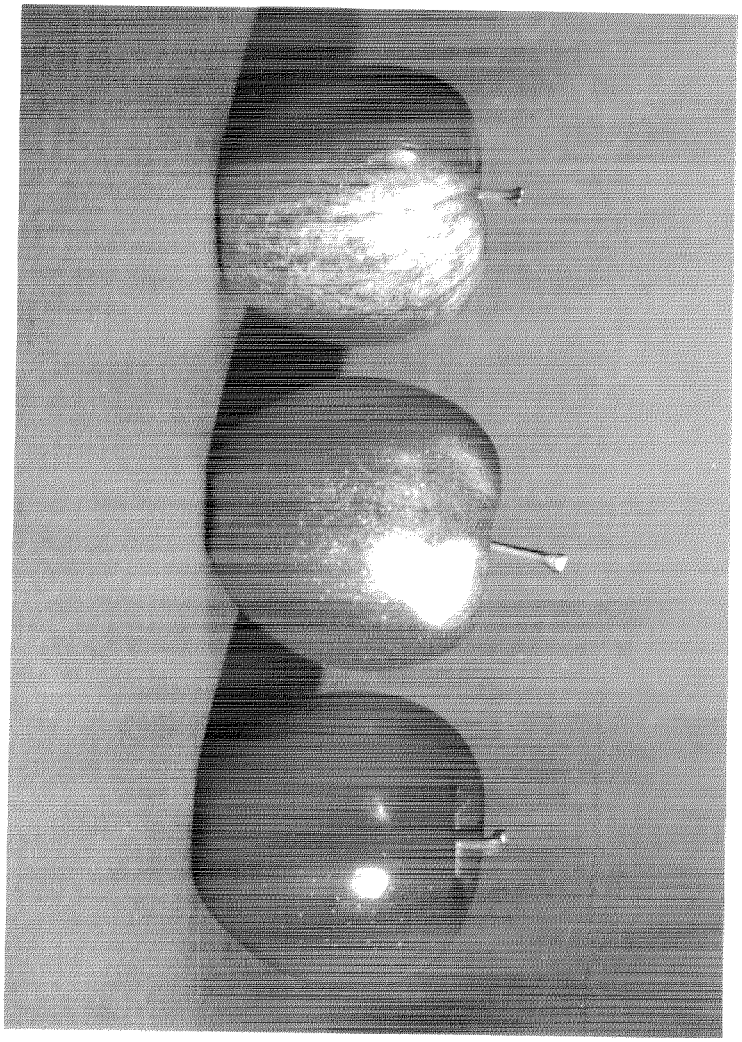
FIG. 2 compares apple color of the Tenroy cv. Gala (left), Waliser cv. Gala (center), and the subject Gale cv. Gala (right).
Figure 3:
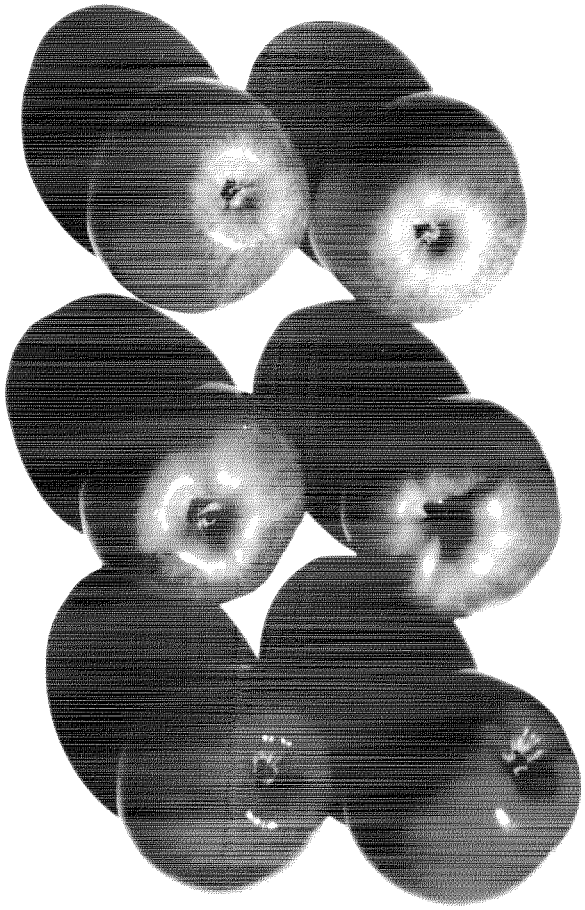
FIG. 3 compares apple calyx end coloration of the Tenroy cv. Gala (left), Waliser cv. Gala (center), and the subject Gale cv. Gala (right).
Figure 4:
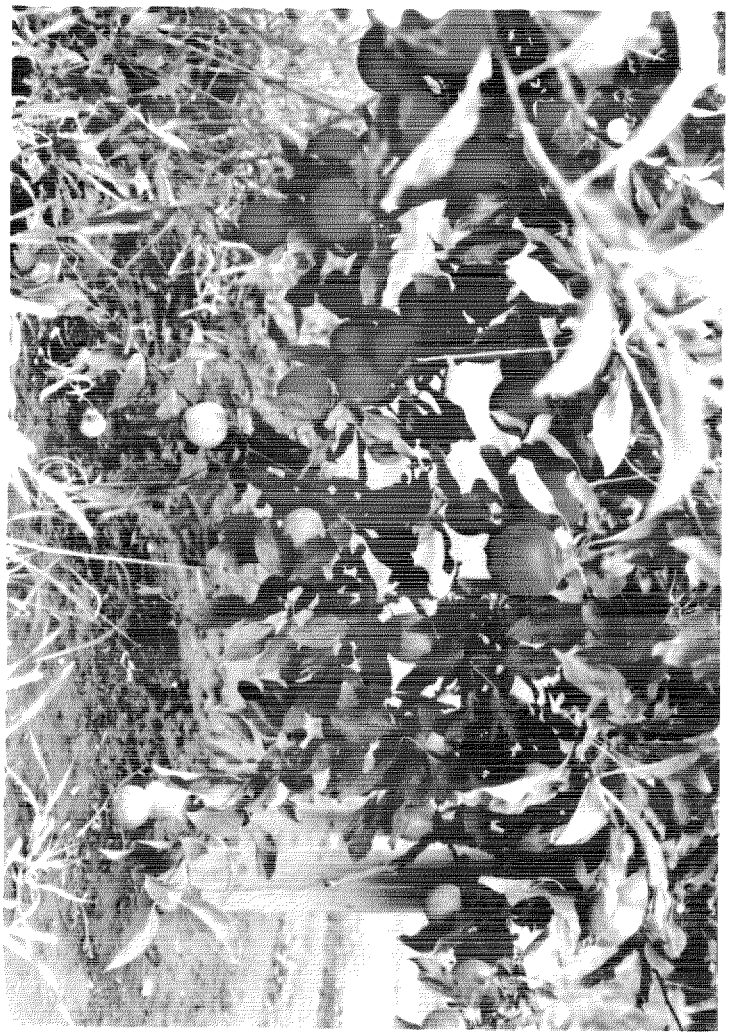
FIG. 4 shows the advanced apple coloration of this new variety (left) compared to the Tenroy cv. Gala (right).
Figure 5:
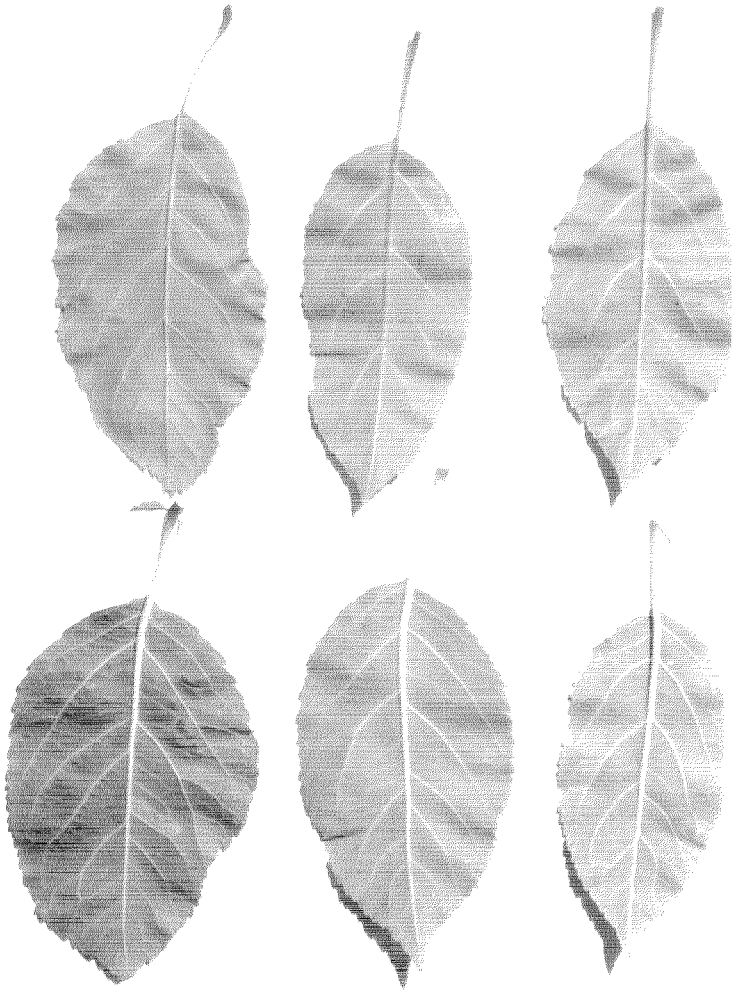
FIG. 5 shows the red midvein on the underside of leaves of the new variety (top) as compared to the Tenroy cv. Gala (bottom).

The new variety has been compared to the parent tree, Royal Gala® (Tenroy cv.). These comparisons included field tests at the Gale orchard in Malaga and at Van Well Nursery scion orchards in East Wenatchee, Wash. Extensive testing of apple pressures and soluble solids between Gale Gala and Tenroy cv. were conducted at Columbia Fruit Packers and Skookum, Inc., both at Wenatchee, Wash. Color comparisons were made at Van Well Nursery offices at Wenatchee.

The apple undercolor of the new variety is 98 to 100 percent full Carmine Red (Plate I, Hue #1, Tone i) on the sun-exposed portion of the fruit and 98 to 100 percent full Nopal Red (Plate I, Hue #3, Tone i) on the shaded side of the fruit, as illustrated in Ridgway's *Color Standards and Color Nomenclature*. The color in the lower third of the stem cavity is Pyrite Yellow (Plate IV, Hue #23, Tone i), according to Ridgway. The apple bears dark red striping, covering approximately 75 to 80 percent of the fruit. This striping is Ox-Blood Red (Plate I, Hue #1, Tone k) from Ridgway. The small lenticels are Maize Yellow (Plate IV, Hue #19, Tone f).

The stem is Garnet Brown (Plate I, Hue #3, Tone I). The full red color extends to the calyx.

In contrast, Tenroy Gala bears a green-yellow undercolor with red-orange striping covering roughly three-quarters (78 percent; see U.S. Plant Pat. No. 7,396) of the fruit. The new variety has a red undertone, as described above, with dark red striping covering.

The flesh color of the new variety and its parent differ as well. Tenroy cv. bears flesh Ivory Yellow (Plate XXX, Hue #21, Tone f), while the new variety bears flesh Marguerite Yellow (Plate XXX, Hue #23, Tone f).

Another distinct difference is the advance coloring of the new variety during the growing season compared to Tenroy cv. The new variety colors ahead of its parent by three weeks when comparing adjacent trees at Mr. Gale's Malaga orchard. Full red color was evident on the new variety by June 22. Waliser cv. colors ten days ahead of Tenroy cv., about eleven days after the new variety.

Although the new variety colors ahead of Tenroy cv., the fruit matures four days after that of Tenroy Gala. Table 1 illustrates this observation, based on starch and soluble solids tests taken by Columbia Fruit.

TABLE 1

| | 8/16/95 | | 8/22/95 | | 8/30/95 | |
|---|---|---|---|---|---|---|
| | Soluble Solids | Starch | Soluble Solids | Starch | Soluble Solids | Starch |
| Gale Gala | 13.4 | 2.65 | 14.4 | 2.43 | 14.8 | 3.16 |
| Royal Gala | 13.6 | 3.0 | 14.4 | 3.9 | 13.6 | 3.8 |

The starch iodine test is used to determine the rate of apple maturation. The Royal Gala comparison chart, which was used, was taken from maturity data system developed by Stemilt Testing Laboratory of the State of Washington. Apples were considered mature at starch contents of at least 2.5–3.5 with soluble solids of about 12 and above.

Leaf color distinguishes the new variety from the Waliser cv. The Waliser cv. exhibits darker green color in the leaves compared to Tenroy cv. The comparisons were made between Waliser Gala (U.S. Plant Pat. No. 8,763) and Tenroy Gala trees of similar age, growing adjacent to each other with similar cultural and environmental factors. The new variety bears leaves with green color identical to its parent, Tenroy cv., and therefore exhibits the same differences in green leaf color to Waliser Gala as Tenroy Gala.

The pinkish-red color of some of the leaf petioles and midribs of Waliser Gala is slightly more pronounced and intense than that of Tenroy cv., and often extends further down the midrib than red color on leaf petioles and midribs produced on the Tenroy cv. The new variety has a longer red midvein in the leaf than Waliser or Tenroy, as illustrated in the accompanying photograph. Unlike Waliser cv. and Tenroy cv., the new variety exhibits red color almost the entire length of the leaf's midvein.

Storage tests conducted on apples of the new variety and Tenroy cv. show other differences. On Sep. 3, 1994, apples of the new variety and Tenroy cv. were placed in controlled atmosphere storage and held. Samples of each apple were removed from storage on Jan. 12, 1995 (Table 2, Sample 1). Pressures and soluble solids were the same at that time (Table 2). Two more samples were removed from storage on Mar. 20, 1995 (Table 2, Sample 2). Apples of the new variety were finn with white flesh, while the parent sample (Tenroy cv.) was mealy and flat.

TABLE 2

| | Tenroy Gala Sample 1 | Tenroy Gala Sample 2 | Gale Gala Sample 1 | Gale Gala Sample 2 |
|---|---|---|---|---|
| Pressure | 14½–15 | 13½–13 | 14½–15 | 14¾–16½ |
| Soluble Solids | 14½–15 | 14½–14 | 14–13 | 14½–13½ |
| Size | 2.81 | 3.20 | 3.90 | 3.50 |

On Mar. 23, 1994, pressure and soluble solids for apples of the new variety and Tenroy cv. were taken from samples kept in regular storage at Skookum, a fruit-packing cooperative located in Wenatchee, Wash. The results are shown in Table 3. The data demonstrate a definite difference in storage quality for the two varieties. Apples of the new variety were firm and less shriveled than the parent. Also, the flesh color of the new variety is lighter in color than that of its parent after emerging from storage. The flesh of the Tenroy cv. was very yellow, compared to the whiter flesh of the new variety.

TABLE 3

| | Tenroy Gala Sample 1 | Tenroy Gala Sample 2 | Gale Gala Sample 1 | Gale Gala Sample 2 |
|---|---|---|---|---|
| Pressure | 10–10¼ | 11–12½–13½ | 12–13–14 | 14–16–16¼ |
| Soluble Solids | 14–14 | 15–15½ | 15½–16¼ | 16½–16 |
| Fruit Size | 125 | 100 | 100 | 100 |

The taste of the two varieties following the Skookum trial was quite dissimilar. The Tenroy cv. was mealy and flat, while the new variety retained a firm texture and sweet taste after seven months in storage.

Color comparisons of apples of the new variety also were made with apples of the Olsentwo Gala (Pacific Gala) variety using the Munsel Limited Color Cascade Standard. Stored apples of similar maturity were compared. The undercolor of apples of the new variety ranged from 40-13 to 39-14, a deeper red color than the Olsentwo apples which ranged from 40-11 to 38-12. There was a marked difference in striping between the two varieties. Apples of the new variety have much wider striping ranging from 1/16th inch, more often 1/8th inch to about ¼ inch and in some instances as much as ½ inch. The Olsentwo striping is fine. Striping of the new variety is darker in color, ranging from 39-15 to 40-15, as compared to Olsentwo striping color range of 39-14 to 40-14, with the differences being even more noticeable due to the wide stripe of the new variety.

Another distinctive difference between the apple of the Olsentwo and the new variety is the coloring of the calyx end. The calyx end of the Olsentwo is often green or light red, ranging from 29-9 to 35-10 in the apples tested. The new variety has a deeper red coloring in the calyx end of the fruit, completely colored with a color of 40-12.

In side-by-side viewing, the most distinctive differences in coloration are the solid red calyx of the new variety as compared to the green or light red calyx end of the Olsentwo, and the deeper red undercolor and broader dark stripes of the new variety as seen for example in FIG. 1.

Other differences between the new variety and the Olsentwo variety are found based on the description in U.S. Plant Pat. No. 9,681. The Olsentwo variety is stated to color 10 days ahead of Tenroy cv. (Column 2, line 43 to Column 3, line 2), as compared to the new variety which colors approximately three weeks ahead of Tenroy cv. Ripening for the Olsentwo cv. is indicated to occur two days ahead of Tenroy cv. (see the paragraph beginning at Column 3, line 35) as compared to the new variety for which the fruit matures four days after that of Tenroy cv. The wood of Tenroy cv. is stated to have a slightly lighter color block than that seen with the Tenroy cv. (see the paragraph beginning at Column 3, line 13), as compared to the new variety for which the wood is similar to that of the Tenroy cv.

DETAILED BOTANICAL DESCRIPTION OF THE TREE

Parentage: Whole tree mutation of Royal Gala® Tenroy cv. (U.S. Plant Pat. No. 4,121) discovered at Malaga, Wash., in cultivated Royal Gala® block by Wallace F. Gale.

Maturity date: August 22–24 at Malaga, Wash.

Tree: Medium size; medium vigorous; dense; upright; round-topped; rapid growing; hardy; productive; regular bearer.

Susceptibility to insects: Medium (similar to other Gala varieties).

Susceptibility to diseases: Medium (susceptible to mildew).

Trunk: Medium; smooth.

Branches: Medium thickness; gray; tan lenticels of medium size.

Flowers: Similar to parent, Tenroy cv.

Buds: Small; short; conical-plump.

Leaves: Similar to Tenroy cv; medium size; average length: about 4 inches; average width about 2 inches; thick; dark green; smooth; crenate, finely serrate; medium petiole, length approximately 1 inch to 1-1¼ inches. differing from Tenroy in midvein being red almost entire length of leaf.

Flowers: Similar to Tenroy cv.; medium timing; medium size; white petals with pink each side; sterile; many flower clusters similar to Gala.

Fruit: Colors evenly and requires fewer picks; undercolor 98 to 100 percent Carmine Red; overstriping 75 to 80 percent Ox-Blood Red; early; medium to small size; round to conical; smooth; symmetrical; hangs well; stores and ships well; date of ripening/coloring as described; long (1-1¼ inch) slender stem.

*Calyx.*—Medium depth and width; symmetrical cavity; closed; small; short lobed.

*Basin.*—Medium; smooth; symmetrical.

*Skin.*—Medium, smooth; waxy; glossy.

*Dots.*—Small; obscure; medium number; round.

*Flesh.*—Firm; crisp; juicy; subacid; white.

*Seeds.*—Similar to Tenroy cv.

*Flavor.*—Typical of Gala.

Use: Fresh, dessert.

Color date: Full red color evident June 22; all fruits color at same time to deep red described herein.

I claim:

1. A new and distinct variety of apple tree substantially as herein shown and described.

* * * * *

UNITED STATES PATENT AND TRADEMARK OFFICE

CERTIFICATE OF CORRECTION

PATENT NO. : PP 10,114
APPLICATION NO. : 08/585500
DATED : November 11, 1997
INVENTOR(S) : Wallace F. Gale It is certified that error appears in the above-identified patent and that said Letters Patent is hereby corrected as shown below:

Titlepage,
Item (54), "APPLE TREE NAMED 'GALE GALA'"
Should read
--APPLE TREE NAMED 'MALAGA'--

Column 1,
Line 28, "Gale Gala" should read --Malaga--;
Line 33, "Gale Gala" should read --Malaga--;

Column 2,
Line 11, "Gale" should read --Malaga--;
Line 15, "Gale" should read --Malaga--;
Line 29, "Gale Gala" should read --Malaga--;

Column 3,
Table 1
Line 7 (of Table 1), "Gale Gala" should read --Malaga--;

Column 4,
Table 2
Line 4 (of Table 2), "Gale Gala" should read --Malaga--;
Line 4 (of Table 2), "Gale Gala" should read --Malaga--;

UNITED STATES PATENT AND TRADEMARK OFFICE

CERTIFICATE OF CORRECTION

PATENT NO. : PP 10,114
APPLICATION NO. : 08/585500
DATED : November 11, 1997
INVENTOR(S) : Wallace F. Gale It is certified that error appears in the above-identified patent and that said Letters Patent is hereby corrected as shown below:

Column 4,
Table 3
Line 4 (of Table 3), "Gale Gala" should read --Malaga--; and
Line 4 (of Table 3), "Gale Gala" should read --Malaga--.

Signed and Sealed this

Twenty-sixth Day of September, 2006

JON W. DUDAS
*Director of the United States Patent and Trademark Office*